(12) United States Patent
Liu et al.

(10) Patent No.: US 10,815,287 B2
(45) Date of Patent: Oct. 27, 2020

(54) ACYLATED DERIVATIVE OF HUMAN INSULIN OR ANALOGUE THEREOF

(71) Applicant: JIANGSU HENGRUI MEDICINE CO., LTD., Lianyungang (CN)

(72) Inventors: Deyu Liu, Lianyungang (CN); Hongwei Wang, Lianyungang (CN); Liang Zhao, Lianyungang (CN); Feifei Wang, Lianyungang (CN); Xiang Zeng, Lianyungang (CN); Tao Wang, Lianyungang (CN); Yali Wang, Lianyungang (CN); Yulu Dai, Lianyungang (CN)

(73) Assignee: JIANGSU HENGRUI MEDICINE CO., LTD., Lianyungang (CN)

( * ) Notice: Subject to any disclaimer, the term of this patent is extended or adjusted under 35 U.S.C. 154(b) by 0 days.

(21) Appl. No.: 16/320,997

(22) PCT Filed: Aug. 1, 2017

(86) PCT No.: PCT/CN2017/095377
§ 371 (c)(1),
(2) Date: Jan. 25, 2019

(87) PCT Pub. No.: WO2018/024186
PCT Pub. Date: Feb. 8, 2018

(65) Prior Publication Data
US 2019/0169257 A1 Jun. 6, 2019

(30) Foreign Application Priority Data

Aug. 2, 2016 (CN) .......................... 2016 1 0625257
Aug. 31, 2016 (CN) .......................... 2016 1 0779132

(51) Int. Cl.
*A61K 38/28* (2006.01)
*A61K 47/54* (2017.01)
*C07K 14/62* (2006.01)
*C07K 1/06* (2006.01)
*C07K 1/107* (2006.01)
*A61P 3/10* (2006.01)

(52) U.S. Cl.
CPC .............. *C07K 14/62* (2013.01); *A61K 38/28* (2013.01); *A61K 47/542* (2017.08); *A61P 3/10* (2018.01); *C07K 1/06* (2013.01); *C07K 1/107* (2013.01); *Y02P 20/55* (2015.11)

(58) Field of Classification Search
CPC ...... A61K 38/28; A61K 47/54; A61K 47/542; C07K 14/62
See application file for complete search history.

(56) References Cited

U.S. PATENT DOCUMENTS

| | | | |
|---|---|---|---|
| 6,310,038 B1* | 10/2001 | Havelund | A61K 9/0075 514/6.3 |
| 2003/0224973 A1* | 12/2003 | Bayer | A61K 38/28 435/6.1 |
| 2011/0105720 A1* | 5/2011 | Madsen | C07K 14/62 530/303 |
| 2014/0328943 A1* | 11/2014 | Havelund | A61K 38/28 424/641 |
| 2014/0329745 A1* | 11/2014 | Sun | C07K 14/62 514/5.9 |

FOREIGN PATENT DOCUMENTS

| | | |
|---|---|---|
| CN | 86106574 A | 8/1988 |
| CN | 101784563 A | 7/1996 |
| CN | 1133598 A | 10/1996 |
| CN | 1829738 A | 9/2006 |
| CN | 101389650 A | 3/2009 |
| CN | 101784563 A | 7/2010 |
| CN | 106496322 A | 3/2017 |
| CN | 106496322 A | 3/2017 |
| EP | 2784085 A1 | 10/2014 |
| WO | 2005012347 A2 | 2/2005 |
| WO | WO2007074133 A2 | 7/2007 |
| WO | 2013086927 A1 | 6/2013 |

OTHER PUBLICATIONS

International Search Report dated Sep. 13, 2017, for PCT Application No. PCT/CN2017/095377, 16 pages. (English Translation).

* cited by examiner

Primary Examiner — Jeffrey E. Russel
(74) Attorney, Agent, or Firm — Morrison & Foerster LLP (57) ABSTRACT

Provided is an acylated derivative of human insulin or an analogue thereof. Specifically disclosed is an acylated derivative of a human insulin analogue, or zinc complex thereof; the human insulin analogue being derivatized is preferably Des(B30) human insulin; the acylated derivative is longer-lasting than existing insulin analogues and acylated derivatives thereof, its blood glucose reduction is more steady, and it is more stable in storage.

20 Claims, 3 Drawing Sheets
Specification includes a Sequence Listing.

ACYLATED DERIVATIVE OF HUMAN INSULIN OR ANALOGUE THEREOF

CROSS REFERENCE TO RELATED APPLICATIONS

This application is a national stage application under 35 U.S.C. § 371 of International Application No.: PCT/CN2017/095377, filed internationally on Aug. 1, 2017, which claims priority to Chinese Application No.: 201610779132.8, file Aug. 31, 2016 and Chinese Application No.: 201610625257.5, filed, Aug. 2, 2016.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 750442000100SEQLIST.TXT, date recorded: Jan. 25, 2019, size: 2 KB).

FIELD OF THE INVENTION

The present invention relates to an acylated derivative of human insulin analogue.

BACKGROUND OF THE INVENTION

Diabetes Mellitus (DM) is a common metabolic endocrine disease, characterized by the absolute or relative lack of insulin in body, or chronic hyperglycemia caused by insensitivity of the target tissue to insulin, DM is clinical chronic, systemic metabolic syndrome accompanied by disorder in carbohydrate, fat and protein metabolism. It is caused by the interaction between genetic and environmental factors, involving various systems of human body, including cardiovascular and cerebrovascular, kidney, eye, nerve and other organ complications, which seriously endanger human health and DM is a lifelong disease.

Diabetes has become a common and frequently-occurring disease. It is the third most human life-threatening disease, following cancer and cardio- and cerebrovascular diseases. It poses a challenge for all human beings, and does harm to people's life and health, regardless of race and nation. According to the International Diabetes Federation (IDF), the total number of people with diabetes was four-fold increased from mid-1980s to mid-1990s, and up to 120 million. In 2007, the number of people with diabetes worldwide was 246 million, of which 46% were laboring population of 40-59 years old. It is estimated that by 2025, the number of diabetic patients worldwide will be increased to 380 million, accounting for 7.1% of the world's adult population.

The use of human insulin is a major method of treating diabetes, but the short action duration of human insulin makes it necessary to inject frequently for patients, which is extremely inconvenient. Therefore, people make effort to obtain insulin analogue and derivative thereof that can act in human body for a longer period of time. Among them, the modification of human insulin or analogue thereof by using acylated groups is an effective method to increase its half-life. WO2005012347 and WO2013086927 disclose two different types of acylated derivatives of human insulin analogue respectively. Such derivatives are obtained by covalently linking acylated group formed by fatty acids to amino acids of the human insulin analogue, and after such modification, their half-life is greatly improved when compared with existing insulin analogues. However, there is still a need to provide insulin analogues or acylated derivatives thereof with longer half-life to enhance the therapeutic effect and also maintain stable blood glucose. Moreover, the existing acylated insulin also suffers from instability, and also there is a need to provide a much stable insulin analogue or acylated derivative thereof.

On the other hand, physiological need for insulin refers to basic time and mealtime (fast-acting), the former provides full-day blood glucose control, and the latter mainly responds to the increase of postprandial blood glucose. According to its physiological characteristics, the ideal mealtime insulin preparation can quickly reach peak after meal, and blood glucose can be reduced to the basic level when blood glucose drops to normal level to avoid hypoglycemia before next meal. The ideal basic insulin should have a very long duration of action (>24 h in all patients), minimal amplitude of insulin variability (to reduce hypoglycemia) and safety, and can be combined with fast-acting insulin (for convenience). Due to the rapid effect of fast-acting insulin on reducing blood glucose, it is required to provide a relatively gentle hypoglycemic effect when combined with basic insulin, so as to avoid the risk of hypoglycemia when they work together. Therefore, it is a very urgent need to provide basic insulin having sufficiently long action period and lowering blood glucose gently at the initial action.

SUMMARY OF THE INVENTION

One object of the present invention is to provide a novel acylated derivative of human insulin analogue, which has a longer lasting effect of lowering blood glucose and has higher stability.

The present invention provides an acylated derivative of human insulin analogue or a zinc complex thereof, wherein said acylated derivative of human insulin analogue has a structure represented by the following formula:

$$S-W-X-Y-Z \qquad (I)$$

wherein S is human insulin in which threonine at amino acid 30 on B chain is absent; —W—X—Y—Z is acylated modifying group of insulin analogue;
wherein W is diacyl structure having —OC(CH$_2$)$_n$CO—, wherein n is an integer between 2 and 10, and an amide bond is formed by one of the structure's acyl groups with α-amino group of amino acid residue at N-end of A-chain or B-chain of parent insulin or analogue thereof or with ε-amino group of lysine residue present on B-chain;
X is a diamino compound containing carboxylic acid group, and an amide bond is formed by linking one of the amino groups of the compound to one of the acyl groups in W;
Y is -A(CH$_2$)$_m$—, wherein m is an integer between 6 and 32, preferably an integer between 10 and 16, particularly preferably an integer between 12 and 14, A is absent or CO—;
Z is —COOH.

Preferably, an amide bond is formed by W with the ε-amino group of lysine residue present on B-chain. Preferably, n is an integer between 2 and 5, preferably 2.

The human insulin in which threonine at amino acid 30 on B chain is absent is a human insulin analogue, the amino acid sequences of A- and B-chain thereof are shown as follows:

A-chain: GIVEQCCTSICSLYQLENYCN, SEQ ID NO. 1

B-chain: FVNQHLCGSHLVEALYLVCGERGFFYTPK. SEQ ID NO. 2

The diamino compound containing carboxylic acid group represented by X is —HN(CH$_2$)$_p$CH(COOH)NH—, wherein p is an integer between 2 and 10, preferably an integer between 2 and 6, particularly preferably an integer between 2 and 4, most preferably 4.

In a preferred embodiment of present invention, —W—X—Y—Z has a structure shown as the following:

(IIa)

preferably is (IIb)

The acylated derivative of human insulin analogue which is particularly preferred in the present invention can be customarily named as N$^\alpha$—(HOOC(CH$_2$)$_{14}$CO)—N$^\varepsilon$—(OCCH$_2$CH$_2$CO—(N$^{\varepsilon B29}$-Des(B30) human insulin))-Lys-OH, having specific structure shown as the following formula (Ia):

(Ia)

Preferably, lysine B29 (N$^\varepsilon$—(N$^\alpha$-hexadecane diacid-L-lysine-N$^\varepsilon$-oxobutyryl))des(B30) human insulin, having structure shown as the following formula (Ib):

The invention also provides a method for preparing the acylated derivative of human insulin analogue or a zinc complex thereof described above, comprising a step of reacting the compound of formula (III) with human insulin in which threonine at amino acid 30 on B chain is absent, wherein R is leaving group, preferably activated ester group, more preferably selected from the group consisting of Preferably, the specific structure of the compound of formula (III) can be shown as (IIIa) or (IIIb):

Said preparation method further comprises a step of removing carboxyl protecting group from compound of formula to obtain compound of formula (III), wherein X' and Z' represent the form that every carboxyl group of X and Z is respectively protected by protecting group, said protecting group is preferably $C_1$-$C_6$ alkyl group, preferably $C_1$-$C_4$ alkyl group, particularly preferably methyl or tert-butyl; and R is as defined in formula (III).

In a particularly preferred embodiment of the invention, the zinc complex of acylated derivative of human insulin analogue is a hexamer of acylated derivative of human insulin analogue, wherein each hexamer contains more than 4 zinc atoms, i.e. the acylated insulin contains more than 4 zinc atoms per 6 acylated insulin molecules; more preferably 5 to 8 zinc atoms, particularly preferably 5 zinc atoms.

The present invention also provides a pharmaceutical composition comprising the aforementioned acylated derivative of human insulin analogue or zinc complex thereof, and a pharmaceutically acceptable carrier.

The present invention also provides the use of the aforementioned acylated derivative of human insulin analogue or zinc complex thereof or pharmaceutical composition thereof for the preparation of a medicament for treating diabetes.

The present invention also provides a pharmaceutical composition, in addition to the aforementioned acylated derivative of human insulin analogue or zinc complex thereof, also comprising fast-acting insulin.

The present invention also relates to the use of the aforementioned acylated derivative of human insulin analogue or zinc complex thereof, or a pharmaceutical composition containing the same, for the preparation of a medicament for treating diabetes.

The present invention also relates to the use of the aforementioned acylated derivative of human insulin analogue or zinc complex thereof, or a pharmaceutical composition containing the same, in combination with fast-acting insulin for the preparation of a medicament for treating diabetes.

Further, the present invention provides a method for treating diabetes, which comprises administering to a patient in need of treatment the aforementioned acylated derivative of human insulin analogue or zinc complex thereof, or a pharmaceutical composition containing the same.

The present invention provides another method for treating diabetes, comprising administering to a patient in need of treatment the aforementioned acylated derivative of human insulin analogue or zinc complex thereof, or a pharmaceutical composition containing the same, as well as fast-acting insulin. The present invention also relates to the aforementioned acylated derivative of human insulin analogue or zinc complex thereof, or a pharmaceutical composition containing the same, as a medicament for treating diabetes.

The present invention also relates to the aforementioned acylated derivative of human insulin analogue or zinc complex thereof, or a pharmaceutical composition containing the same, in combination with fast-acting insulin, as a medicament for treating diabetes.

Diabetes in the present invention includes type I diabetes and type II diabetes.

DETAILED DESCRIPTION OF THE DRAWINGS

DETAILED DESCRIPTION OF THE INVENTION

The invention is further described below in conjunction with the examples.

Example 1

Preparation of lysine B29 (N$^\varepsilon$—(N$^\alpha$-hexadecane diacid-L-lysine-N$^\varepsilon$-oxobutyryl))des(B30) Human Insulin 1. Preparation of N$^\alpha$-(hexadecane diacid)-N$^\varepsilon$-(3-acylpropionic acid-OSu) lysine

X15

X01 (150 g, 524.5 mmol) was taken; dry THF (2.5 L) was added at room temperature, then a catalytic amount of DMF (1.0 mL) was added; oxalyl chloride (49 mL) was added into a 100 mL constant-pressure dropping funnel; oxalyl chloride was slowly dropwise added into the reaction flask for about two hours, during which gas was generated, and it was necessary to continuously degas. After the completion of dropwise addition, the mixture was stirred at room temperature for 1.5 hr, then THF was subjected to vacuum rotary evaporation; and DCM (800 mL) and tert-butanol (500 mL) were added to the reaction flask and stirred at room temperature overnight. The tert-butanol and dichloromethane were subjected to vacuum rotary evaporation, and dichloromethane (1 L) was added and filtered to remove insoluble solid. The filtrate was subjected to vacuum rotary evaporation and then brought to flow through the column. The desired fractions were collected, dried by rotary evaporation, and recrystallized from petroleum; 54 g of product X02 was harvested, meanwhile di-tert-butyl ester product X03 was recovered.

X02 (28.5 g, 83.3 mmol) was dissolved in DCM (200 mL). N-hydroxy-succinimide (5.54 g, 48.1 mmol) and di-isopropyl-carbodiimide (7.6 mL) were added at room temperature, and stirred at room temperature for one day. TLC indicated the substantial completion of reaction. The reaction mixture was filtered to remove insoluble solid. The solvent was removed by vacuum rotary evaporation. The purification was performed by column chromatography, and 28.5 g of X04 was obtained.

X04 (22 g, 50.1 mmol) was dissolved in dry THF (250 mL), and stirred at room temperature. Lysine derivative (20.5 g, 55 mmol) and tri-ethylamine (21 mL) were added to the reaction system respectively and stirred at room temperature for 24 h. The mixture was filtered through diatomite, and washed by THF for 3 times. The solvent was removed by vacuum rotary evaporation. The purification was performed by column chromatography, and 31 g of X11 was obtained.

X11 (30.6 g, 46.3 mmol) was dissolved in anhydrous ethanol (200 mL), stirred at room temperature. 6.0 g of 10% Pd/C was then added, and hydrogen was added; the reaction was performed at room temperature overnight, with stirring vigorously. The mixture was filtered through diatomite, and washed by anhydrous ethanol for 3 times. The filtrate was subjected to vacuum rotary evaporation. 24.5 g of crude product X12 was obtained and directly used for the next reaction.

X12 (24 g, 45.6 mmol) was dissolved in dried THF (200 mL), and tri-ethylamine (12.7 mL) was added. After that, the temperature was decreased to 0° C. Succinic anhydride (5.2 g, 52 mmol) was added into the reaction system in batches, and stirred for another 30 min at 0° C. And then, the reaction system was transferred to room temperature and stirred overnight. THF was removed by vacuum rotary evaporation. The residue was dissolved in dichloromethane (500 mL), washed twice by 5% citric acid solution (500 mL*2), and washed once by saturated salt solution. The mixture was dried against anhydrous sodium sulfate. The solvent was removed by vacuum rotary evaporation. 29.0 g of crude X13 was obtained and directly used for the next reaction.

X13 (28.5 g, 45.5 mmol) was dissolved in DCM (200 mL). N-hydroxy-succinimide (5.54 g, 48.2 mmol) and di-isopropyl-carbodiimide (7.6 mL) were added at room temperature and stirred at room temperature for one day. TLC indicated the substantial completion of reaction. The reaction mixture was filtered to remove insoluble solid. The solvent was removed by vacuum rotary evaporation. The purification was performed by column chromatography, and 28.5 g of X14 was obtained.

X14 (3.0 g, 4.1 mmol) was dissolved in trifluoroacetic acid (15 mL), and stirred at room temperature for 45 min, then trifluoroacetic acid was removed by vacuum rotary evaporation at low temperature. When anhydrous diethyl ether was added, solid was precipitated and filtered. The filtrate mass was washed by anhydrous diethyl ether for three times. The solid was dried, and 1.8 g of product X15 was obtained.

2. Preparation of lysine B29 ($N^\varepsilon$—($N^\alpha$-hexadecane diacid-L-lysine-$N^\varepsilon$-oxobutyryl)) des(B30) Human Insulin 53 mg human insulin (with threonine at 30th aa on B chain absent) (8 mg/mL, 50 mM Tris HCl pH 8.5 buffer) was taken, pH was adjusted to about 10.75 with 1.5 M $Na_2CO_3$, and then the concentration was adjusted to 4 mg/mL by using buffer (50 mM Tris HCl pH 8.5 buffer). $N^\alpha$-(hexadecane diacid)-$N^\varepsilon$-(3-acylpropionic acid-OSu) lysine (18 mg) was suspended in 7 mL of acetonitrile; 1.75 mL of this solution was added to the above mentioned human insulin (with threonine at amino acid 30 on B chain absent) every 15 min to initiate the reaction; the addition of this solution was completed in 4 portions with stirring. After the addition was completed, timing was started. After 1 h of reaction, the solution pH was adjusted to about 7.5 with acetic acid, and the reaction was terminated to obtain a crude solution. The reaction process was in-process controlled by RP-HPLC.

3. Purification of lysine B29 ($N^\varepsilon$—($N^\alpha$-hexadecane diacid-L-lysine-$N^\varepsilon$-oxobutyryl)) des(B30) Human Insulin The above crude precursor solution was diluted with water to make content of organic phase to about 15% (v:v), and filtered through a 0.45 μm filter, and purified by RP-HPLC to obtain a purified liquid.

4. Ultrafiltration and Lyophilization of lysine B29 ($N^\varepsilon$—($N^\alpha$-hexadecane diacid-L-lysine-$N^\varepsilon$-oxobutyryl))des(B30) Human Insulin The sample contained in above purified solution was replaced into water for injection by using an ultrafiltration membrane package system, and was lyophilized to obtain 26 mg of the lyophilized product. The structure formula of the obtained molecule is as follows:

Formula (Ib)

5. Structural Confirmation of lysine B29 ($N^\varepsilon$—($N^\alpha$-hexadecane diacid-L-lysine-$N^\varepsilon$-oxobutyryl))des (B30) Human Insulin The measured mass spectrum molecular weight of lysine B29 ($N^\varepsilon$—($N^\alpha$-hexadecane diacid-L-lysine-$N^\varepsilon$-oxobutyryl)) des(B30) human insulin is 6203.37 Da, which is consistent with the theoretical molecular weight of 6203.21 Da.

INS was subjected to enzymatic hydrolysis with V8 protease, and hydrolyzed product was analyzed by LC-MS analysis, the result shows that a total of 4 peptide fragments were produced with molecular weights of 416.23 Da (A1-A4), 2968.29 Da (A5-A17, B1-B13), 1376.57 Da (A18-A21, B14-B21) and 1510.84 Da (B22-B29) respectively, which correspond to the theoretical peptide fragment molecular weight, wherein the peptide fragments B22-B29 are fatty acid chain-modified peptide fragment. It is proven that the modification site is consistent with expectation.

Example 2: Investigating the Hypoglycemic Effect of Agent to be Tested on STZ-Induced Type I Diabetes Model 1. Samples to be Tested

| Name | Agent to be tested (INS-1) | Agent to be tested (INS-2) | Insulin degludec |
|---|---|---|---|
| Supplier | JIANGSU HENGRUI | JIANGSU HENGRUI | Novo Nordisk |
| Physical state | colorless liquid | colorless liquid | colorless liquid |
| Storage condition | 4° C. | 4° C. | 4° C. |

Among them, INS-1 and INS-2 represent two different complexes prepared from lysine B29 ($N^\varepsilon$—($N^\alpha$-hexadecane diacid-L-lysine-$N^\varepsilon$-oxobutyryl))des(B30) human insulin, wherein each insulin derivative hexamer comprises 5 Zn and 8 Zn, respectively. The preparation method is a conventional method in the art, and each hexamer in insulin degludec contains 5 Zn.

2. The Formulation of Samples to be Tested

Samples to be tested were stored at 4° C. in the dark, and an appropriate amount of 600 nmol/mL stock solution of each test sample was taken. Each Sample was diluted 400-fold with solvent to reach 1.5 nmol/mL, and the dosage was 7.5 nmol/kg. The agent was returned to room temperature before use.

3. Experimental Animals

| Species | SD rat |
|---|---|
| Grade | SPF animal |
| Week-old when ordered | 6-week |
| Week-old when experiment started | 8-9-week |
| Body Weight range | 300-400 g |
| Gender | male |
| Supplier | Silaike Experimental animal Co., Ltd. |
| Supplier address | Shanghai, China |
| Animal identification method | Labeled on tail by marker |
| Numbers of animals ordered | 50 |
| Numbers of animals used | 40 |

4. Experimental Method

SPF grade rats were maintained in laboratory environment for 7 days, and provided with standard feeding, standard cage at temperature of 20-25° C. with humidity of 40-60%. One day before the model was established, the rats were fasted for 16 hours, and STZ (65 mg/kg) was quickly injected into abdominal cavity. After 1 hour, the rats were provided with food. After the model was established, plenty of daily water (providing the amount of drinking water 2-3 times higher than normal) and food is provided; bedding was changed 1-2 times per day to keep dry. Fasting blood glucose was measured on day 5 (fasting for 6 hours) and rats with a blood glucose value >16.7 mmol/L were selected. According to the blood glucose level, they were divided into 4 groups.

Animal grouping and administration information are as follows:

| Groups | Animal type | Animal number | Dosing dosage (nmol/kg) | Dosing volume (mL/kg) | Administration route | Administration frequency |
|---|---|---|---|---|---|---|
| Solvent control | STZ rat | 10 | / | 5 | SC | once |
| Insulin degludec | STZ rat | 10 | 7.5 | 5 | SC | once |
| INS-1 | STZ rat | 10 | 7.5 | 5 | SC | once |
| INS-2 | STZ rat | 10 | 7.5 | 5 | SC | once |

The rats were not fasted before administration, and single dose of each agent was injected subcutaneously. The control group was injected with the same volume of solvent. All rats were fasted after administration till the end of experiment. The blood glucose levels in rats were measured at 1, 2, 4, 6, 8, 10, 12, and 24 hours after administration. After the blood glucose level was measured at 24 hours, blood was collected to prepare serum.

All data was entered into an Excel document and expressed as Mean±SEM. Data statistical analysis was performed using Graphpad Prism 6.0 software by one-way or two-way ANOVA analysis, with P<0.05 as a standard for significant difference.

5. Results:

On day 5 after injection of STZ, SD rats were fasted for 6 hours and blood glucose was measured to confirm 80% success rate of model establishment.

Figure 1:
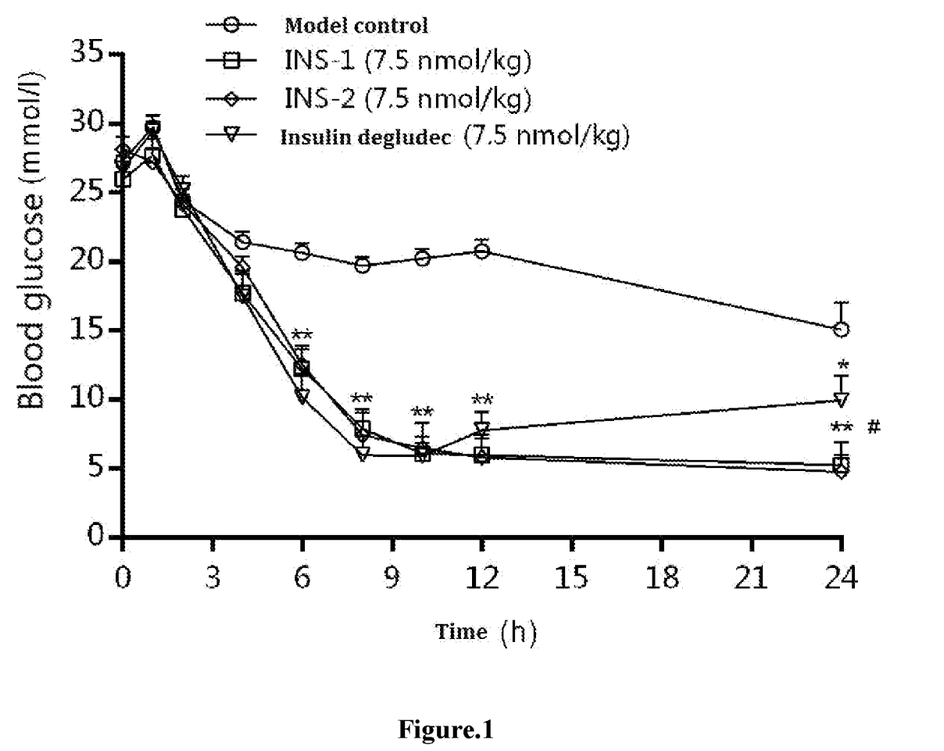
FIG. 1 is a curve showing the change in blood glucose level after administration in STZ rats (*P<0.05, **P<0.01 vs model control group; # P<0.05 vs insulin degludec).

It can be seen from FIG. 1 that the basic blood glucose level in STZ solvent group was 27.3 mmol/L before administration, and the blood glucose level was gradually decreased after administration, reaching 15.1 mmol/L after 24 hours, and the change of blood glucose value was 12.1 mmol/L. In positive group of insulin degludec administration, the change of blood glucose value before and after administration was 16.8 mmol/L. The blood glucose levels in the group of positive agent insulin degludec were significantly different from those in solvent group of negative control at 6, 8, 10, 12 and 24 hours after administration, indicating the effectiveness of animal model and experimental method.

Compared with the solvent group of negative control, the agents to be tested, both INS-1 and INS-2 significantly reduced the blood glucose level in animals within 24 hours after administration, and significant differences at 6, 8, 10, 12 and 24 hour time points were observed; In addition, the blood glucose level continued to be decreased, indicating that the agents have good long-acting hypoglycemic effect.

As for test agents INS-1 and INS-2, the curves showing the change of blood glucose values along with the time after administration in STZ rats were basically consistent, indicating that the hypoglycemic effects of the two agents were similar. At the time point of 24 hours, the hypoglycemic effects of INS-1 and INS-2 were better than that in insulin degludec group, indicating that INS-1 and INS-2 have better long-acting effect.

Example 3: Investigating the Hypoglycemic Effects of Various Long-Acting Insulins on STZ-Induced Type I Diabetes Models 1. Samples to be Tested

| Name | INS-A | INS-B | INS-C | Insulin degludec |
|---|---|---|---|---|
| Supplier | JIANGSU HENGRUI | JIANGSU HENGRUI | JIANGSU HENGRUI | Novo Nordisk |

-continued

| Name | INS-A | INS-B | INS-C | Insulin degludec |
|---|---|---|---|---|
| Physical state | colorless liquid | colorless liquid | colorless liquid | colorless liquid |
| Storage condition | 4° C. | 4° C. | 4° C. | 4° C. | wherein INS-A represents for HS061 in WO2013086927, INS-B represents for HS067 in WO2013086927, and INS-C represents for lysine B29 ($N^\epsilon$—($N^\alpha$-hexadecane diacid-L-lysine-$N^\epsilon$-oxobutyryl)) des(B30) human insulin, all samples to be tested shared the same formulation, and were in the form of zinc complex, with each insulin hexamer containing 5 Zn.

2. Formulation of Samples to be Tested

Samples to be tested were stored at 4° C. in the dark, and an appropriate amount of 600 nmol/mL stock solution of the test sample was taken. Each sample was diluted 80-fold with solvent to 7.5 nmol/mL, and the dosage was 7.5 nmol/kg. The agent was returned to room temperature before use.

3. Experimental Animals

| | |
|---|---|
| Species | SD rat |
| Grade | SPF animal |
| Week-old when ordered | 6-week |
| Week-old when experiment started | 8-9 week |
| Body Weight range | 300-400 g |
| Gender | male |
| Supplier | Beijing Vital River Laboratory Animal Technology Co., Ltd |
| Supplier address | Beijing, China |
| Animal identification method | Label on tail by marker |
| Numbers of animals ordered | 60 |
| Numbers of animals used | 40 |

4. Experimental Method

SPF grade rats were maintained in laboratory environment for 7 days, and provided with standard feeding, standard cage at temperature of 20-25° C. with humidity of 40-60%. One day before the model was established, the rats were fasted for 16 hours, and STZ (65 mg/kg) was quickly injected into abdominal cavity. After 1 hour, the rats were provided with food. After the model was established, plenty of daily water (providing the amount of drinking water 2-3 times higher than normal) and food is provided; bedding was changed 1-2 times per day to keep dry. Fasting blood glucose was measured on day 5 (fasting for 6 hours) and rats with a blood glucose value >16.7 mmol/L were selected. According to the blood glucose level, they were divided into 5 groups.

Animal grouping and administration information are as follows:

| Groups | Animal type | Animal number | Dosing dosage (nmol/kg) | Dosage volume (mL/kg) | Administration route | Administration frequency |
|---|---|---|---|---|---|---|
| Solvent control | STZ rat | 8 | / | 1 | SC | once |
| Insulin degludec | STZ rat | 8 | 7.5 | 1 | SC | once |
| INS-A | STZ rat | 8 | 7.5 | 1 | SC | once |
| INS-B | STZ rat | 8 | 7.5 | 1 | Sc | once |
| INS-C | STZ rat | 8 | 7.5 | 1 | Sc | once |

The rats were not fasted before administration, and single dose of each agent was injected subcutaneously. The control group was injected with the same volume of solvent. All rats were fasted after administration until the end of experiment. The blood glucose levels in rats were measured at 1, 2, 4, 6, 8, 10, 12, and 24 hours after administration.

All data was entered into an Excel document and expressed as Mean±SEM. Data statistical analysis was performed using SPSS software by one-way or two-way ANOVA analysis, with $P<0.05$ as a standard for significant difference.

5. Results:

The basic blood glucose value in STZ solvent group was 27.01 mmol/L before administration, and the blood glucose value was gradually decreased after administration, reaching 11.64 mmol/L after 24 hours, and the change of blood glucose value was 15.37 mmol/L. The change of blood glucose value before and after administration in positive group of insulin degludec, was 19.78 mmol/L. The blood glucose levels in the group of positive agent insulin degludec were significantly different from those in solvent group of negative control at 1, 2, 4, 6, 8, 10 and 12 hours after administration, indicating the effectiveness of animal model and experimental method.

Compared with the solvent group of negative control, the agents to be tested, INS-A, INS-B and INS-C significantly reduced the blood glucose level in animals within 24 hours after administration. As seen from the blood glucose values, the blood glucose values in test agent groups (7.03±1.15, 3.57±0.44, and 4.20±0.72 mmol/L, respectively) were lower than that in solvent negative control group (11.64±3.94 mmol/L). This indicates that all three agents have relatively good long-acting hypoglycemic effect. The differences were especially compared among groups at 0 to 6 hours. The particular values are shown in Table 1 and Table 2:

TABLE 2

AUC values of blood glucose within 0 to 2, 0 to 4 and 0 to 6 hours after single administration (Mean ± SEM, n = 8)

| Group | Blood glucose AUC value (mmol/L · h) | | |
|---|---|---|---|
| | 0~2 h | 0~4 h | 0~6 h |
| Insulin degludec | 39.92 ± 1.35$^{\$\$}$ | 57.24 ± 3.54$^{\$}$ | 62.49 ± 3.84$^{\$}$ |
| INS-A | 38.17 ± 1.09$^{\$\$}$ | 50.93 ± 2.96$^{\$\$}$ | 55.03 ± 3.34$^{\$\$}$ |
| INS-B | 39.52 ± 1.40$^{\$\$}$ | 56.56 ± 3.49$^{\$}$ | 61.74 ± 4.40$^{\$}$ |
| INS-C | 45.42 ± 1.25 | 69.52 ± 3.74 | 76.81 ± 5.09 |

Note:
$^{\$}P < 0.05$,
$^{\$\$}P < 0.01$ vs INS-C.

Figure 2:
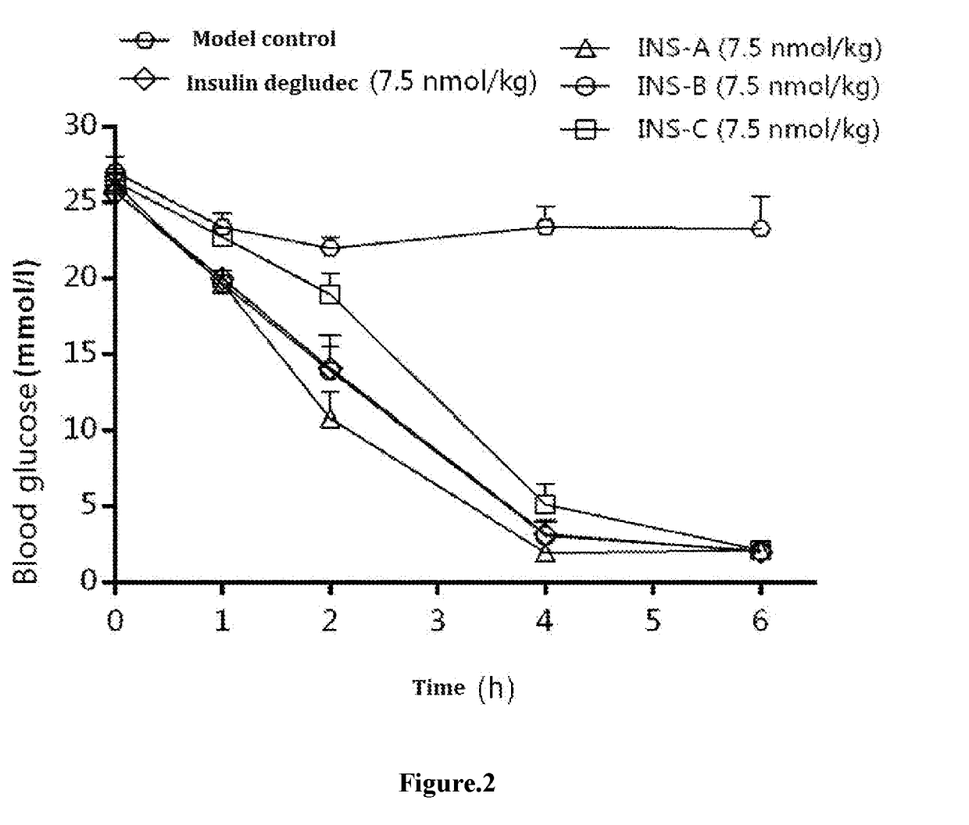
FIG. 2 is a curve showing the change of blood glucose level within 0-6 hours after administration in STZ rats.
Figure 3:
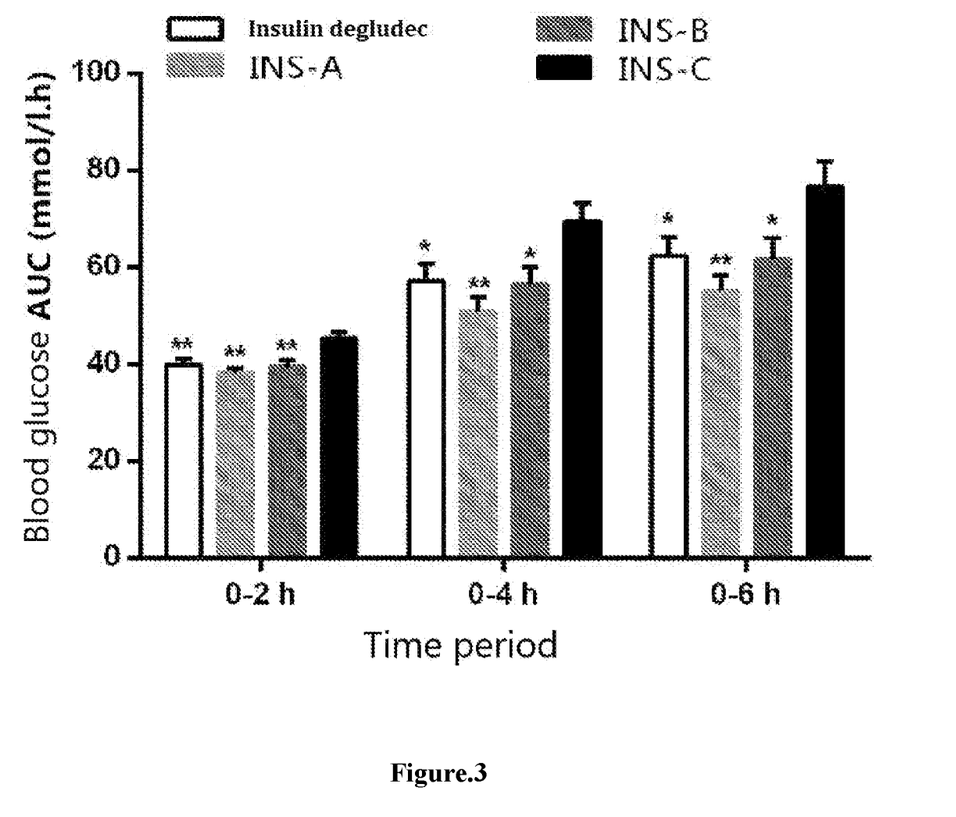
FIG. 3 shows the comparison of blood glucose AUC, 0 to 2, 0 to 4 and 0 to 6 hours after administration (*P<0.05, **P<0.01 vs INS-C).

As for INS-C and insulin degludec, the blood glucose value of STZ rats in INS-C group was decreased less than that in insulin degludec group after administration, and was significantly higher than that in insulin degludec group 1 hour after administration (see FIG. 2 and Table 1). The particular values are shown in Table 1. As can be seen from FIG. 3 and Table 2, the areas under the blood glucose-time curves (AUC) within 0 to 2, 0 to 4 and 0 to 6 hours after administration of INS-C were all significantly higher than those of insulin degludec. This suggests that, when administered in combination with fast-acting insulin or formulated as compound composition, INS-C+fast-acting insulin has a significantly lower risk of hypoglycemia than that of insulin degludec+fast-acting insulin within 0-6 hours after administration (the period during which the fast-acting insulin exerts hypoglycemic effect).

As for INS-C and INS-A, the blood glucose value of STZ rat in INS-C group was decreased less than that in INS-A group after administration, and was significantly higher than that in INS-A group 1, 2 and 4 hours after administration; but

TABLE 1

Effect of single administration on blood glucose in STZ-induced type I diabetes rats (Mean ± SEM, n = 8)

| | Blood glucose value (mmol/L) | | | | |
|---|---|---|---|---|---|
| Group | before administration | 1 h after administration | 2 h after administration | 4 h after administration | 6 h after administration |
| Solvent | 27.01 ± 1.02 | 23.41 ± 0.89 | 22.01 ± 0.71 | 23.43 ± 1.32 | 23.30 ± 2.09 |
| Insulin degludec | 25.69 ± 0.72 | 20.01 ± 0.75**$^{\$}$ | 14.13 ± 2.16** | 3.20 ± 0.81** | 2.05 ± 0.16** |
| INS-A | 26.19 ± 0.71 | 19.68 ± 0.55**$^{\$\$}$ | 10.80 ± 1.77**$^{\$\$}$ | 1.96 ± 0.33**$^{\$}$ | 2.14 ± 0.23** |
| INS-B | 25.73 ± 0.73 | 19.69 ± 0.86**$^{\$\$}$ | 13.94 ± 1.59**$^{\$}$ | 3.10 ± 1.02** | 2.09 ± 0.22** |
| INS-C | 26.38 ± 0.87 | 22.75 ± 0.51 | 18.96 ± 1.37 | 5.14 ± 1.36** | 2.15 ± 0.15** |

Note:
*$P < 0.05$,
**$P < 0.01$ vs blank solvent group;
$^{\$}P < 0.05$,
$^{\$\$}P < 0.01$ vs INS-C.

was significantly lower than that in INS-A group 10 and 12 hours after administration; the blood glucose value 24 hours after administration also tends to be lower than that in INS-A group. It indicates that INS-C has a slower hypoglycemic rate than that of INS-A, but better long-acting effect than that of INS-A, and INS-C is more suitable for the characteristics of long-acting insulin. In addition, as can be seen from FIG. 3, the blood glucose AUC of INS-C was significantly higher than that of INS-A within 0 to 2, 0 to 4 and 0 to 6 hours after administration. This suggests that, when administered in combination with fast-acting insulin or formulated as compound composition, INS-C+fast-acting insulin has a significantly lower risk of hypoglycemia than that of INS-A+fast-acting insulin within 0-6 hours after administration.

As for INS-C and INS-B, the blood glucose value of STZ rats in INS-C group was decreased less than that in INS-B group after administration, and was significantly higher than that in INS-B group 1 and 2 hours after administration, indicating that INS-C has a slower hypoglycemic rate than that of INS-B. In addition, as can be seen from FIG. 3, the blood glucose AUCs of INS-C were all significantly higher than those of INS-B within 0 to 2, 0 to 4 and 0 to 6 hours after administration. This suggests that, when administered in combination with fast-acting insulin or formulated as compound composition, INS-C+fast-acting insulin has a significantly lower risk of hypoglycemia than that of INS-B+fast-acting insulin within 0-6 hours after administration.

Combining the hypoglycemic effect within 24 hours and that within 0 to 6 hours, INS-C was characterized by long-lasting hypoglycemic effect and gently hypoglycemic effect at initial phase. It is the most ideal long-acting insulin, and is especially suitable for the administration in combined with fast-acting insulin or formulated as compound composition, in order to reduce the number of injections and improve patient compliance.

Example 4: Canine PK Test (INS-B and INS-C have the Same Meaning as Those in Example 3)

Six male beagle dogs (3 in each group) were administered with a single subcutaneous injection of INS-B or INS-C (3 nmol/kg). Blood was collected at different time points, and serum was isolated to detect the concentration of INS-B or INS-C in serum. The results showed that INS-B reached peak at 4.7±1.2 hours (3 animals for 4, 4 and 6 hours, respectively), while INS-C reached its peak at 8 hours (all 3 animals for 8 hours). The half-life of INS-B and INS-C was 6.0±1.2 and 7.8±1.1 hours, respectively. This suggests that the action of INS-C is more gentle and lasts longer.

Example 5: Stability Comparison

INS-A, INS-B, INS-C (each code has the same meaning as that in Example 3) and insulin degludec were formulated according to the marketing prescription of insulin degludec. And then, their stability was examined, the purity of the main peak and the content of impurity at the initial and later time points were determined by HPLC. The particular results are shown in Table 3. As can be seen from Table 3, the stability of INS-C is significantly better than that of INS-A and INS-B; slightly better than that of insulin degludec.

TABLE 3

Comparison data of stability

| Sample to be tested | Condition/duration | % purity of Main peak | Normalized total impurity % |
|---|---|---|---|
| INS-C | 0 day | 99.40 | 0.60 |
| INS-A | | 99.22 | 0.78 |
| INS-B | | 98.48 | 1.52 |
| Insulin degludec | | 99.02 | 0.98 |
| INS-C | 40° C., 7 days | 98.86 | 1.14 |
| INS-A | | 95.86 | 4.14 |
| INS-B | | 94.86 | 5.14 |
| Insulin degludec | | 98.11 | 1.89 |
| INS-C | 55° C., 7 days | 93.15 | 6.85 |
| INS-A | | 52.00 | 48.00 |
| INS-B | | 53.56 | 46.44 |
| Insulin degludec | | 91.67 | 8.33 |
| INS-C | 40° C., 14 days | 98.38 | 1.62 |
| Insulin degludec | | 97.75 | 2.25 |
| INS-C | 55° C., 14 days | 87.94 | 12.06 |
| Insulin degludec | | 86.71 | 13.29 |

Note:
The data on day 14 was no longer measured with respect to INS-A and INS-B groups, since the impurities in these groups were increased too fast on day 7.

What is claimed is:

1. An acylated derivative of human insulin analogue or a zinc complex thereof, wherein the acylated derivative of human insulin analogue has a structure represented by the following formula:

S—W—X—Y—Z    (I)

wherein S is human insulin in which threonine at amino acid 30 on B chain is absent; and
—W—X—Y—Z is an acylated modifying group of the human insulin analogue;
wherein W is a diacyl structure having —OC(CH$_2$)$_n$CO—, wherein n is an integer between 2 and 10, and an amide bond is formed by one of said diacyl structure's acyl groups with an α-amino group of the amino acid residue at N-end of A-chain or B-chain of the human insulin analogue or with ε-amino group of lysine residue present on B-chain;

X is a diamino compound containing a carboxylic acid group, and an amide bond is formed by linking one of the amino groups of the compound to one of the acyl groups in W;
Y is -A(CH$_2$)$_m$—, wherein m is an integer between 6 and 32 and A is absent or CO—; and
Z is —COOH.

2. The acylated derivative of human insulin analogue or a zinc complex thereof according to claim 1, wherein the amide bond is formed by W with the ε-amino group of lysine residue present on B-chain.

3. The acylated derivative of human insulin analogue or a zinc complex thereof according to claim 1, wherein n is an integer between 2 and 5.

4. The acylated derivative of human insulin analogue or a zinc complex thereof of claim 3, where the integer n is 2.

5. The acylated derivative of human insulin analogue or a zinc complex thereof according to claim 1, wherein X is —HN(CH$_2$)$_p$CH(COOH)NH—, wherein p is an integer between 2 and 10.

6. The acylated derivative of human insulin analogue or a zinc complex thereof of claim 5, where the integer p is between 2 and 6.

7. The acylated derivative of human insulin analogue or a zinc complex thereof of claim 6, where the integer p is between 2 and 4.

8. The acylated derivative of human insulin analogue or a zinc complex thereof of claim 7, where the integer p is 4.

9. The acylated derivative of human insulin analogue or a zinc complex thereof of claim 1, where the integer m is between 12 and 14.

10. The acylated derivative of human insulin analogue or a zinc complex thereof according to claim 1, wherein —W—X—Y—Z has a structure shown as the following:

(IIa)

11. The acylated derivative of human insulin analogue or a zinc complex thereof according to claim 1, wherein —W—X—Y—Z has a structure shown as the following:

(IIb)

12. N$^\alpha$—(HOOC(CH$_2$)$_{14}$CO)—N$^\varepsilon$—(OCCH$_2$CH$_2$CH$_2$CO—(N$^{\varepsilon B29}$-Des(B30) human insulin))-Lys-OH or a zinc complex thereof.

13. The acylated derivative of human insulin analogue or a zinc complex thereof of claim 12, wherein the insulin analogue is lysine B29 (N$^\varepsilon$—(N$^\alpha$-hexadecane diacid-L-lysine-N$^\varepsilon$-oxobutyryl))des(B30) human insulin or a zinc complex thereof.

14. The zinc complex of the acylated derivative of human insulin analogue according to claim 1, wherein more than 4 zinc atoms are complexed with every 6 acylated insulin molecules.

15. A pharmaceutical composition comprising the acylated derivative of human insulin analogue or a zinc complex thereof according to claim 1, and a pharmaceutically acceptable carrier.

16. The pharmaceutical composition according to claim 15, further comprising fast-acting insulin.

17. A method for treating diabetes comprising administering to a patient in need thereof the acylated derivative of human insulin analogue or a zinc complex thereof according to claim 1.

18. A method for treating diabetes comprising administering to a patient in need thereof the acylated derivative of human insulin analogue or a zinc complex thereof according to claim 1 in combination with fast-acting insulin.

19. A method for treating diabetes comprising administering to a patient in need thereof the pharmaceutical composition according to claim 15.

20. A method for treating diabetes comprising administering to a patient in need thereof the pharmaceutical composition according to claim 15 in combination with fast-acting insulin.

* * * * *

SEQUENCE LISTING

<160> NUMBER OF SEQ ID NOS: 2

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 29
<212> TYPE: PRT
<213> ORGANISM: Artificial Sequence
<220> FEATURE:
<223> OTHER INFORMATION: Modified B chain of human insulin analogue,
      missing Thr at position 30

```
<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25
```